United States Patent [19]
Rodriguez

[11] Patent Number: 5,973,211
[45] Date of Patent: Oct. 26, 1999

[54] PIGMENTING EFFICIENCY OF A NATURAL XANTHOPHYLL BY ISOMERIZATION

[75] Inventor: Gustavo Rodriguez, Sinaloa, Mexico

[73] Assignee: Prodemex, S.A. DE C.V., Mexico

[21] Appl. No.: 08/896,878

[22] Filed: Jul. 18, 1997

[51] Int. Cl.[6] .................................................. C07C 35/08
[52] U.S. Cl. .......................... 568/834; 568/816; 568/822; 568/823; 568/824; 568/825; 568/832; 568/906; 568/913
[58] Field of Search .................................. 568/834, 816, 568/822, 823, 824, 825, 832, 906, 913

[56] References Cited

U.S. PATENT DOCUMENTS

| | | | |
|---|---|---|---|
| 3,523,138 | 8/1970 | Grant | 260/617 |
| 3,841,967 | 10/1974 | Jaroslav et al. | 195/29 |
| 3,891,504 | 6/1975 | Schocher et al. | 195/28 R |
| 3,951,743 | 4/1976 | Shepherd et al. | 195/28 R |
| 3,989,757 | 11/1976 | Surmatis | 260/598 |
| 4,048,203 | 9/1977 | Philip | 260/412.8 |
| 5,019,668 | 5/1991 | Keat et al. | 585/364 |
| 5,382,714 | 1/1995 | Khachik | 568/834 |
| 5,523,494 | 6/1996 | Torres-Cardona et al. | 568/834 |
| 5,648,564 | 7/1997 | Ausich et al. | 568/834 |

FOREIGN PATENT DOCUMENTS

| | | |
|---|---|---|
| 9402253 | 3/1994 | Mexico . |
| 1046658 | 10/1966 | United Kingdom . |
| WO 96/02594 | 2/1996 | WIPO . |

OTHER PUBLICATIONS

Isomerization of Carotene to B–Carotene and of Lutein to Zeaxanthin, A.G. Andrewes, Short Communications from Acta Chem. Scand. B 28, (1974) No. 1.

Separation of Zeaxanthin and Lutein via the Dicarbamates of Ethyl Isocyanate, A. Ruttimann et al., Journal of High Resolution Chromatography and Chromatography Communications, vol. 6, Nov. 1983, pp. 612–616.

Carotenoids of Higher Plants, A. G. Andrewes et al., Short Communications from Acta Chem. Scand. B28 (1974), No. 1.

The First Isolation of Enanthiomeric and Meso–Zeaxanthin in Nature, Takashi Maoka et al., Comp. Biochem. Physiol., vol. 83B, No. 1, pp. 121–124, 1986.

*Primary Examiner*—Cecilia J. Tsang
*Assistant Examiner*—C. Delacroix-Muirheid
*Attorney, Agent, or Firm*—Knobbe, Martens, Olson, Bear, LLP

[57] ABSTRACT

A method of isomerizing lutein to yield a mixture of epimers of zeaxanthin includes the following steps: mixing a lutein-containing extract in a glycol solution to obtain a mixture, treating the mixture with alkali to obtain an alkali-containing mixture, reacting the alkali-containing mixture in the presence of heat for a duration consistent with achieving a desired level of isomerization of lutein to zeaxanthin.

22 Claims, 2 Drawing Sheets

PIGMENTING EFFICIENCY OF A NATURAL XANTHOPHYLL BY ISOMERIZATION

BACKGROUND OF THE INVENTION

1. Field of Invention

The present invention relates to chemical processes to yield zeaxanthin-like isomers, and more particularly, to the reactions of a naturally derived lutein pigment in the presence of polyhydric alcohols and alkali. The present invention also relates to the products produced by these synthetic methods, as well as the methods of using the pigments thus produced.

2. Description of Related Art

Carotenoids belong to an important class of natural pigments responsible for the coloration of many plant and animal species. These pigments are commonly used as coloring agents in food stuffs. In particular, adequate coloration is a major concern in the poultry industry where certain levels of pigmentation appeal to the consuming public.

To meet the expectations of the consumer, poultry producers have traditionally supplemented the diet of poultry with carotenoid containing meals of plant origin. The pigments extracted from these natural plants are capable of producing the desired yellow-orange color in poultry and poultry products, such as, in the skin of broiler chickens and egg yolks. A common plant source of carotenoids is marigold meal.

The family of carotenoid pigments consists of hydrocarbons, or carotenes, and of oxygenated carotenoids, or xanthophylls. In particular, it is the hydroxycarotenoids, or xanthophylls that have been shown to be most effective in attaining the desired level of pigmentation for use in poultry and poultry products. Lutein, a hydroxycarotenoid, is one of the most abundant, and widely used, natural carotenoids found commonly in marigold meal and its extracts.

Lutein, as well as other oxycarotenoids, occur naturally as esters of fatty acids, mainly as palmitic, myristic and stearic esters. However, the pigmenting efficiency of these xanthophylls are known to be increased in their free form where the ester linkage has been broken by means of a saponification reaction. Thus, saponification is generally performed following extraction of xanthophylls.

Various methods have been utilized to prepare xanthophyll concentrates from marigold meal. For example, in U.S. Pat. No. 3,523,138, marigold meal is reacted with an alcoholic alkali solution to remove the ester linkage. Following this saponification reaction, the mixture is generally solvent extracted to yield xanthophyll. Also, as described in U.S. Pat. No. 3,783,099, enzymatic hydrolysis of the cellulosic material of marigold meal can improve the extraction of the xanthophylls.

Carotenoids derive their intense color from the presence of a chain of conjugated double bonds in the chromophore. Moreover, it is the precise configuration of double bonds within the chromophore that gives different carotenoids their particular shades of yellow, orange or red. For instance, trans lutein, produces a yellow color with an absorbance maximum at 474 nm in hexane. If, however, trans luetin is isomerized, with only a single change in position of a conjugated double bond, an orange pigment is obtained with an absorbance maximum of 478 nm in hexane. Thus, in terms of the relative pigmenting efficiency, zeaxanthin yields more color per unit of pigment.

Although lutein is the predominate hydroxycarotenoid derived from marigold meal, it is its structural isomer, zeaxanthin, that has been shown to be more effective as a pigment, as compared to lutein, due to the precise bonding structure within the zeaxanthin chromophore. Typical extraction procedures of hydroxycarotenoids from marigold meal, however, yield approximately 82–88% of the less effective lutein and only about 3–6% of the more effective, zeaxanthin pigment.

More recently, fermentation reactions have been described in which alternative strains of *Flavobacterium Multivorum* result in production of zeaxanthin extracts with a 2 to 3 fold higher pigmenting efficiency, as compared with plant carotenoids, as described in PCT Int. Appl., WO91 03,571, dated Mar. 21, 1991 and issued to Applied Biotechnology, Inc. Generally however, the common source for zeaxanthin pigment is yellow corn and yellow gluten.

Chemical methods also have been described which result in the isomerization of lutein to zeaxanthin. Karrer and Jucker have described reacting lutein in the presence of sodium ethoxide and benzene to yield zeaxanthin. Karrer and Jucker, *Helv. Chem. Acta*, vol. 30, 366 (1947). Andrewes has also reported the isomerization of lutein to zeaxanthin under nitrogen, in the presence of methanol, potassium methoxide, and dimethylsulfoxide. A. G. Andrewes, *Acta Chem. Scand.*, vol. B28, No. 1, 1137 (1974). Both reactions resulted in low yields. Consequently, these reaction processes are not suitable for industrial application.

Interestingly, Andrewes, et al., suggested that the reaction products can consist of several stereoisomers, rather than the trans zeaxanthin which is found in natural pigment sources. A. G. Andrewes, G. Borch, and S. Iiaaen-Jensen, *Acta Chem. Scand.*, vol. B28, No. 1, 139 (1974). More recently, Maoka, et al., has confirmed the presence of three stereoisomers upon reaction of lutein in the presence of hydroxide. These include two optical isomers and a meso compound, namely (3R,3'R)-zeaxanthin, or trans zeaxanthin, (3S,3'S)-zeaxanthin, and (3R,3'S)-zeaxanthin. T. Maoka, A. Arai, M. Shimizu & T Matsuno, *Comp. Biochem. Physiol.*, vol. 83B, No. 1, 121 (1986). Separation of these stereoisomers of zeaxanthin has also been reported. A. Ruttimann, K. Schiedt, and M. Vecchi, J. High Resolution Chromatography & Chromatography communications, Vol. 6, 612 (1983). The relative pigmenting efficiency of these stereoisomers, however, is unknown.

These reported reactions of lutein in the presence of a strong base and an organic solvent are generally considered to be catalytic, and require the absence of water or humidity. The presence of water in such a catalytic organic reactive phase would result in violent exothermic reaction, not suited for ordinary industrial use. However, recently Torres-Cardona, U.S. Pat. No. 5,523,494, disclosed the isomerization of lutein to zeaxanthin in a non-catalytic aqueous phase reaction. In this procedure, lutein is reacted with in a highly alkaline, aqueous solution for long periods of time to yield zeaxanthin. An alkaline, aqueous isomerization reaction also has been reported to lead to greater yields of zeaxanthin when performed under vacuum, as disclosed by Espinoza in Mexican Patent Application No. MX 942253.

Given the higher pigmenting efficiency of zeaxanthin relative to lutein, it would be desirable to produce zeaxanthin in a catalytic reaction suited for ordinary industrial use. Such a reaction would exclude the use of known toxins, such as benzene or dimethylsulfoxide, and would instead utilize non-toxic solvents. If these solvents were also non-aqueous, this should enhance the reaction rate yielding a more efficient overall reaction.

Therefore, there exists a need to synthetically produce zeaxanthin or a zeaxanthin-like pigment via an environmentally safe and economically efficient method suitable for industrial purposes. Moreover, the reaction should not only be temporally efficient in terms of the reaction time, but more importantly, the reaction should be efficient in terms of the yield of zeaxanthin produced per gram of lutein. Finally, the final zeaxanthin, or zeaxanthin-like, pigment should exhibit good stability as reflected in its shelf life.

SUMMARY OF THE INVENTION

The main object of the present invention is to provide processes leading to the isomerization of lutein to zeaxanthin and/or zeaxanthin-like epimer(s). It is an object of the present invention to obtain these products via an efficient catalytic-like reaction which does not utilize toxic organic solvents. The present invention, instead, provides the use of safe glycols as solvents, which are used in the food industry as emulsifiers, to effect the reactions of lutein to yield zeaxanthin(s).

Moreover, the present invention has many advantages over the prior art. The zeaxanthin-enriched products are obtained in higher yields, partially due to greater recovery of the total xanthophyll content. Additionally, the products thus produced show increased pigmenting efficiency per gram in relation to the weight of the starting extract or oleoresin. Importantly, when the reactions of lutein, which include both saponification and isomerization, are conducted in a glycol, increased stabilization of the final product is observed as reflected in its longer shelf life.

An aspect of the present invention includes methods to isomerize lutein to yield a mixture of epimer(s) of zeaxanthin comprising the following steps: (1) mixing a lutein-containing extract in a glycol solution to obtain a mixture; (2) treating said mixture with alkali to obtain an alkali containing mixture; (3) reacting the alkali containing mixture in the presence of heat for a duration consistent with achieving the desired level of isomerization of lutein to zeaxanthin or zeaxanthin-like isomers. The inventive process can also be conducted in the presence of an inert atmosphere, such as nitrogen, or under vacuum.

The inventive processes also can be carried out in two steps. In the first step, alkali is added in a sufficient amount to effectively saponify the lutein mixture. In a second step, alkali is again added in an amount sufficient to effectively isomerize lutein to yield a mixture of zeaxanthin-like isomers. The isomerization step also can be selectively carried out in the presence of an inert atmosphere, such as nitrogen, or under vacuum. In addition, the lutein-containing substrate can be largely in its saponified or esterified form. Further, the lutein-containing extract can contain other xanthophylls.

The amount of alkali added to effect both saponification and isomerization of lutein to yielding increased levels of zeaxanthin and zeaxanthin-like epimer, is generally from about 10% to 50% alkali, by weight, added to the total mixture. Preferably the levels of alkali would be from about 15% to 30% alkali, by weight, added to the mixture. If the saponification and isomerization reactions are conducted in two steps, the first step should include from about 8% to 20% alkali, by weight, and the second step should include from about 1% to 30% alkali, by weight of the final mixture. The methods of the present invention encompass the use of any alkali, such as a metal hydroxide, metal carbonates, ammonium hydroxide, ammonia, an organic base or their mixtures. Preferably, metal hydroxides or their mixtures would be used.

The reaction time can be varied in the present invention to achieve the desired level of isomerization of lutein. Reaction times ranging from about 5 minutes to 300 hours can effect isomerization depending on the amount of total alkali, temperature and pressure utilized. Generally, a reaction time from about 1 hour to 50 hours can be used to effect the reactions of the present invention. However, high levels of isomerization are achieved using reaction times from about 2 to 25 hours, with a reaction time of 3 to 6 hours being preferred.

Also reaction temperature can be varied to achieve the desired level of isomerization of lutein within the desired time frame. Generally, reaction temperature from about 25° C. to 180° C. can be used, however, the preferred reaction temperature range is from about 50° C. to 150° C., with reaction temperature of 60° C. to 120° C. being most preferred. Moreover, if the saponification and isomerization reactions are conducted as separate steps, the reaction temperature of each step can be a different temperature within the ranges given herein.

Although the processes of the present invention can be carried out without the addition of pressure, pressure ranges from about 5 psi to about 150 psi, and atmospheric pressure can be applied if desired. Generally, slight pressure will be present within the reactor due mainly to the nitrogen blanket and the vapor pressure of the glycol.

Significantly the processes of the present invention yield a product enriched in zeaxanthin, or zeaxanthin-like isomers in the range of about 6% to 90% of the total xanthophylls present in the final mixture. Moreover, there are numerous uses for the product thus obtained. These uses include a general use of the product, or its formulations, as a pigment, as well as more specific uses of the product as pigmenting agent for the skins of chickens and egg yolks. This natural product can also be used as an ingredient in food stuffs.

Another aspect of the present invention includes the novel product obtained from the processes of the present invention. Thus, the invention includes the lutein isomerized product containing a mixture of zeaxanthin and zeaxanthin-like isomers. The zeaxanthin-enriched product, described herein, is obtained in yields of from about 6% to 90% zeaxanthin of the total carotenoid content. The zeaxanthin-enriched product typically represents about 10% to 80% of the total carotenoid content, with a yield of from about 20% to 70% being most typical. The products, which consists of epimer(s) of zeaxanthin, are produced by the processes of the invention, and includes isomerizing a lutein-containing extract with alkali and a glycol in the presence of heat for a duration consistent with achieving the desired level of isomerization of lutein.

This zeaxanthin-enriched product can be obtained from the processes of the present invention that are conducted in the presence of an inert atmosphere, such as nitrogen, or under vacuum conditions. Moreover, this product can be obtained starting with a lutein extract that is largely saponified or esterified. The reaction temperatures can range from about 50° C. and 130° C., and reaction times range from about 1 to 20 hours.

These and other objects and advantages of the present invention will be apparent to persons skilled in the art, from the following description of the specific embodiments, represented by examples.

DETAILED DESCRIPTION OF THE PREFERRED EMBODIMENT

The present invention relates to lutein isomerizing processes which yield high levels of a mixture of zeaxanthin-like isomers. The products of this processes exhibit improved pigmenting efficiency as compared with lutein. The novel isomerization reaction is conducted in the presence of a glycol and alkali to yield epimer(s) of zeaxanthin at "catalytic" rates of reaction. Additionally, both a saponification reaction and the isomerization reaction can be conducted in the presence of a glycol yielding a pigment with improved properties. Overall, the methods described herein yield a mixture of zeaxanthin isomers with improved pigmenting efficiency, improved recovery of the total xanthophyll content and greater stabilization of the final products thus produced.

Figure 1:
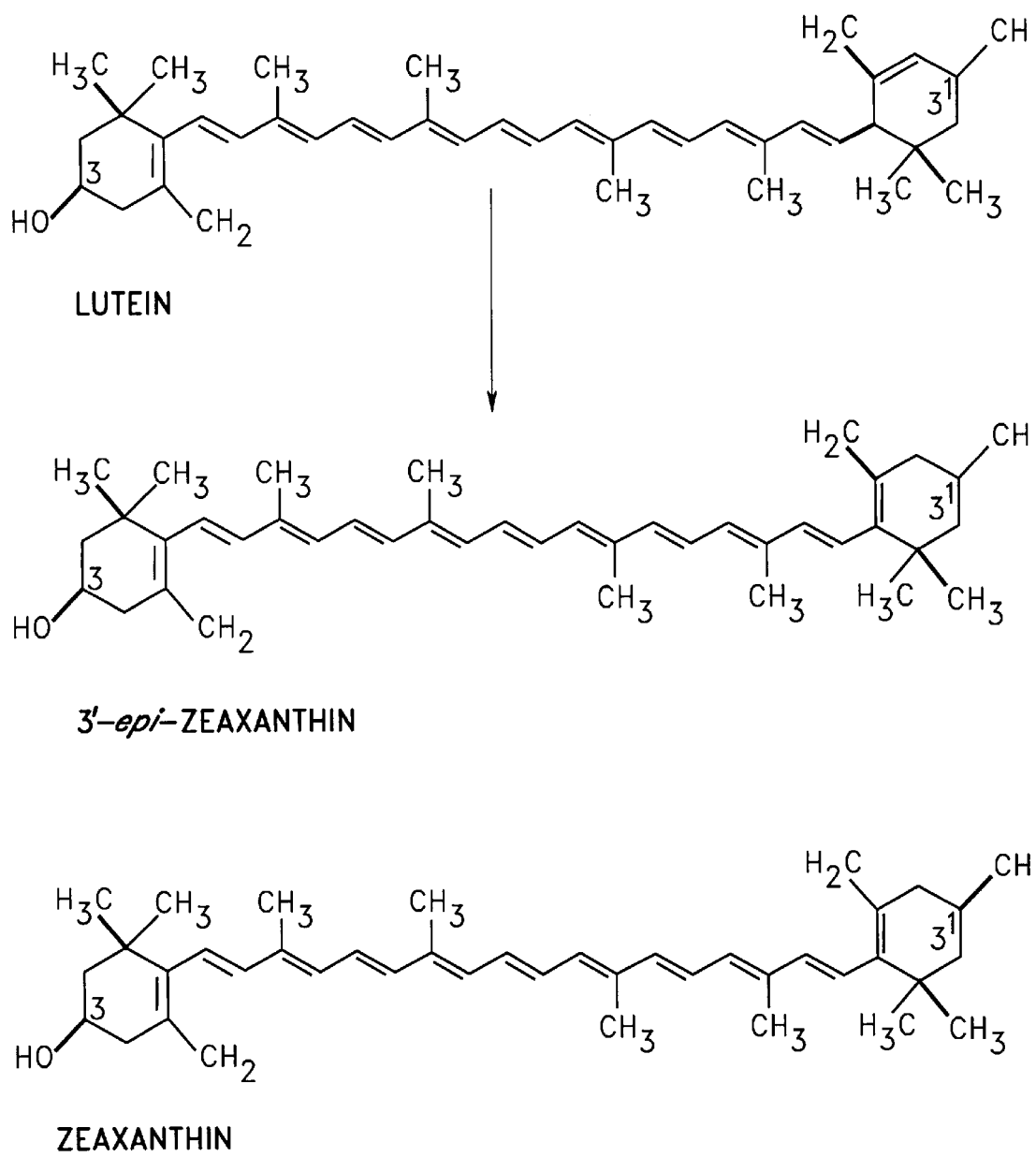
FIG. 1 illustrates the chemical reaction of lutein to yield epimers of zeaxanthin.

FIG. 1 illustrates the reaction of the present invention starting with trans lutein to yield a mixture of 3'-epimers of zeaxanthin. Overall, the inventive processes involve the isomerization of natural trans lutein to a zeaxanthin-like isomer, or mixture of zeaxanthin-like isomers. This zeaxanthin has similar functionality as does the natural trans zeaxanthin when used for the coloration in foods or in the formulation of feeds.

Figure 2:
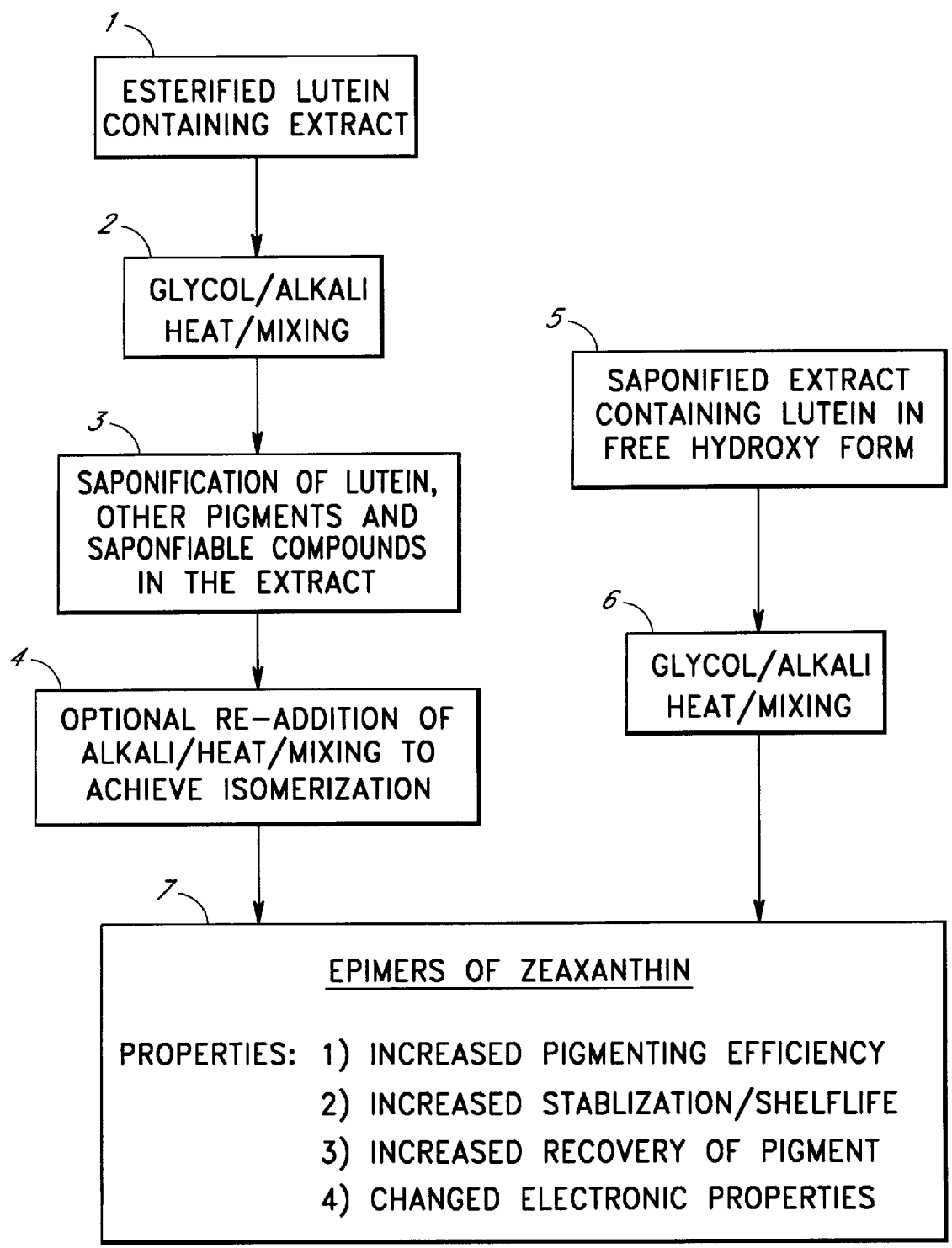
FIG. 2 illustrates the steps and reagents used in the reaction of lutein to yield epimers of zeaxanthin which display novel properties.

FIG. 2 illustrates the steps and reagents leading to the production of these zeaxanthin-like isomers. Preferably, the inventive process is applied by starting with a concentrated pigment extract from any source containing trans lutein, as depicted in 1. Moreover, the trans lutein substrate for the isomerization reaction can be either in the ester form or in the free hydroxy form. It is preferable that saponification of the ester be carried out prior to isomerization of lutein, as depicted in 3.

Reference numeral 2 depicts the addition of alkali and a glycol solution to saponify lutein 3. The extract to be treated is homogenized in a glycol solution, such as propylene glycol, polyethylene glycol, glycerin, etc., using from 0.1 to 1 parts of glycol to 1 part of extract by weight. A mixture of glycols can also be used. In the present invention, however, the preferred reaction solvent is propylene glycol. A weight ratio of glycol to extract of 0.2 to 0.5 is also preferred.

A metal hydroxide, or a combination of alkaline reagents, is then added and the mixture is heated in a closed reaction vessel under nitrogen 2. When using a oleoresin extracted from machine harvested marigold flowers, a mixture of sodium hydroxide and potassium hydroxide is the preferred choice of alkaline reagents. Moreover, the amount of alkali required will vary, depending on the substrate and process conditions utilized. Generally, the total amount of metal hydroxide(s) is in the range of 0.1 to 0.4 parts per part of extract by weight.

The addition of the alkali can be done in two steps. First, enough metal hydroxide is added to achieve saponification of the extract 2. The quantity needed will depend on the saponification index of the extract which can be measured by a saponification number determination (adapted from AOAC Official Methods of Analysis, 15th ed., 920.160 (1990)). Generally, the stoichiometric amount is between 8% to 15% of alkali with respect to the weight of the extract.

The general procedure in the art has been to saponify using an aqueous alkaline solution. The novel reactions of the present invention generally exclude water at both the saponification and isomerization stages. Thus, the inventive processes include saponification of the lutein extract in the presence of glycols.

The temperature used for saponification will depend on the material being saponified, and the saponification step can occur at a temperature lower than that used for the isomerization reaction which follows. The saponification step preferably occurs at a temperature between about 20° C. and about 180° C., more preferably between about 25° C. and 120°, still more preferably between about 40° C. and about 100° C.

In a second step 4, more alkali can be added to effect the isomerization reaction. The amount of alkali required is usually within the range added for the saponification reaction. The alkali can be added in granular form or dispersed in the glycol used for the isomerization reaction. Additionally, the starting material for the isomerization reaction can be a saponified product 5. In this case, only one alkali addition step is required 6.

The rate of the addition can vary, and greatly depends on the reactor mechanism for introduction of reactants. Moreover, when reactants are introduced, it is preferable not to disrupt the nitrogen blanket within the reactor by the introduction of air.

The time of reaction is variable, and largely depends on the actual temperature within the reactor 4. In general, the reactor is preferably operated between about 25° C. and about 180° C., with a reaction temperature from about 50° to about 150° C. being more preferred, temperatures between about 60° and about 120° C. being still more preferred, and a reaction temperature between about 80° C. and about 110° being even more preferred. Generally, the reactions of the present can be conducted using reaction times from about 30 minutes to 5 hours, or until the desired level of isomerization is achieved. The preferred reaction time is from about 3 to 5 hours. Of course, at higher reaction temperatures, the reaction time is shorter.

No additional pressure is required to be applied to the reactor when conducting the reactions of the present invention. The reaction pressure within the chamber is about 5 to 15 psi manometric, due mainly to the nitrogen blanket and the vapor pressure of the glycol solution. Additional pressure can be applied, however, if needed. The novel reactions can also be conducted under vacuum if desired.

After the isomerization reaction is complete, the mixture obtained can be further processed to a powder by drying in the presence of inert ingredients, or to a liquid pigment formulation by emulsifying the mixture by the addition of a surfactant and water. Moreover, the mixture obtained following the isomerization reaction can also be purified to yield a highly concentrated pigment mixture. This purification is accomplished by extracting the pigments with organic solvents and then concentrating by solvent elimination, or another means of concentrating the pigment.

The resultant product mixture contains zeaxanthin-like epimer(s) 7. Moreover, the products yielded by the methods of the present invention exhibit properties which suggest an electronic change has occurred. Thus, both the absorbance and circular dichroic spectra of the resultant product mixture are significantly changed as compared with that of unprocessed lutein.

Additionally, the circular dichroic spectrum appears to indicate the production of a significant amount of the meso isomer of zeaxanthin. Further, the novel reactions of the present invention yield important improvements in pigment recovery and stabilization. Using the novel processes, it is typical to obtain a 5% increase, or greater, in the amount of pigment recovered when glycols are used in lieu of water at the saponification stage. The level of increased recovery of pigment depends largely, however, on the nature and/or origin of the extract used. Thus, pigmenting efficiency per gram of lutein is increased when using the inventive methods. Additionally, greater pigment stability is observed in the final powder form products when the saponification reaction is conducted in glycols. This greater stability is reflected in the extended useful lifetime of the final products, which is apparently due to the slower rate of degradation of the finished powdered pigment.

These improvements in recovery and stabilization are due largely to the nonaqueous reaction milieu provided for in both the saponification and isomerization reactions of the present invention. In contrast, the prior art alkaline, aqueous reactions, which require the presence of metal hydroxides and $H_2O$ can provide a slight buffering capacity to the solution. Thus, in these aqueous reactions, the alkalinity of the reaction solution is decreased relative to nonaqueous condition. On the other hand, the reactions of the present invention are performed in a nonaqueous glycol solution, which serves to increase the overall alkalinity of the reaction solution due to the lack of buffering capacity of glycols. Moreover, since the standard practice in the art is to utilize an oleoresin substrate, which is oily in substance, a reaction conducted in water would present a solubility barrier between the aqueous-soluble alkaline reactants and the nonaqueous-soluble oleoresin substrate.

Finally, the reaction of the present invention does not use dangerous organic solvents, for example, benzene, dimethylsulfoxide, methanol, ethanol, acetone, hexane, etc., all of which present safety and environmental problem in terms of their industrial use. This novel reaction instead utilizes non-toxic and environmentally safe glycol solvents, well-known as food grade emulsifiers. In particular, propylene glycol is regarded as nontoxic, and its oxidized form yields the non-toxic pyruvic and acetic acids. Moreover, the use of a glycol solution produces a reaction mixture and yields products that are very easy to handle in the ordinary industrial setting of a pigment plant.

Significantly, the reaction of the present invention eliminates the need of using water or dispersants, thus allowing the isomerization reaction to attain "catalytic" rates without the introduction of toxic organic solvents. Additionally, these "catalytic" rates are achieved without the application of high pressure to the reaction system. Thus, the reaction times and conditions of the present invention are appropriate for industrial production of a zeaxanthin isomer.

To further illustrate the present invention a set of examples is described below.

EXAMPLES

Example 1

An oleoresin obtained from the hexane extraction of hand-picked dehydrated marigold flowers was saponified following solvent elimination, using 15% sodium hydroxide in granular form, on a weight to weight basis with respect to the desolventized extract. The reaction is begun by first adding 4 kg of oleoresin and then mixing this resin with 1.2 kg of propylene glycol. After 15 minutes of mixing, 0.6 kg of sodium hydroxide was added to initiate saponification. After 50 minutes of reaction at 80° C., another 0.4 kg of alkali were added and subsequently reacted for 3 hours at 110 to 112° C. For this process, saponification was carried out at atmospheric pressure. Following saponification, the second reaction step was performed where the product was isomerized at 5 psi of pressure due mainly to a nitrogen blanket in the contained vessel. For this reaction, mixing was continuous at 40 RPM during both the saponification and isomerization reaction. Using this two-step reaction, an isomerized product was obtained where 33.3% of the total carotenoids were in the zeaxanthin-like form having started with 4.5% of trans zeaxanthin in the raw material.

Example 2

In this case, 30 kg of solvent free extract obtained from mechanically harvested marigold flowers were mixed with 12 kg of propylene glycol in the reactor. The mixture was preheated to 60° C., and once the reactor reached this temperature alkali was added. The alkali consisted of 6 kg of potassium hydroxide, plus 3 kg of sodium hydroxide, which was sufficient for both the saponification and isomerization reactions. The reactions were then carried out for 5 hours at a temperature that fluctuated between 100 to 106° C. A nitrogen pressure of 15 psi was maintained throughout and mixing was continuous at 120 RPM. After the 5 hours of reaction time the level of zeaxanthin isomer obtained was 59.8% relative to total carotenoids. The starting oleoresin had contained 4.8% trans zeaxanthin.

Example 3

For this reaction 4 kg of oleoresin, similar to that described in Example 1, was mixed with 0.6 kg of glycerine and 0.8 kg of propylene glycol. These three ingredients were taken to 65° C., and once this temperature was reached alkali was added consisting of 0.6 kg of potassium hydroxide and 0.4 kg of sodium hydroxide. This alkaline material was sufficient to saponify and isomerize the lutein. Agitation was kept at 44 RPM for the first half hour and then raised to 144 RPM. The total reaction time was 4.5 hours. After addition of the alkali, the temperature was raised to and maintained at from about 95 to 100° C. Also for the first half hour the reactor was operated at atmospheric pressure. For the subsequent four hours, the reactor was maintained at 7 psi pressure. Under these conditions, a natural abundance of 4.5% trans zeaxanthin in the original oleoresin was enriched to 22.7% total zeaxanthin, which is a mixture of zeaxanthin isomers. These percentages are given relative to the total carotenoid content.

Example 4

A batch of 8 kg of saponified marigold oleoresin in stonehard solid form was put into an open reaction chamber. This material was mixed with 3 kg of propylene glycol and 1 kg of glycerine at 65° C. for 90 minutes. Mixing was carried out at 44 RPM. An homogenous paste was obtained and to it 1.2 kg of potassium hydroxide in granular form was added. The chamber was closed and kept at 5 psi after flushing with nitrogen. The temperature was then raised to 100° C.±2° C., and maintained at the same mixing speed. The reaction was run for six hours to achieve isomerization. A five fold increase in zeaxanthin-like isomers was obtained from a starting material that contained 3.8% trans zeaxanthin.

In conclusion, it is noted that these examples are merely given as a means of illustrating the numerous ways that the inventive processes can be implemented. Thus, the use of examples is in no way intended to reflect a limited number of ways of practicing the invention.

What is claimed is:

1. A method of isomerizing lutein to yield a mixture of epimers of zeaxanthin comprising the following steps:

mixing a lutein-containing extract in a non-aqueous glycol solution to obtain a mixture;

treating said mixture with non-aqueous alkali to obtain an non-aqueous alkali-containing mixture;

reacting the non-aqueous alkali-containing mixture in the presence of heat for a duration sufficient to achieve a desired level of isomerization of lutein to zeaxanthin epimers.

2. The method of claim 1, wherein the reacting step is conducted in the presence of an inert atmosphere.

3. The method of claim 2, wherein said inert atmosphere consists essentially of nitrogen.

4. The method of claim 1, wherein the treating step comprises first adding a sufficient amount of non-aqueous alkali to saponify the mixture, and second adding an additional amount of non-aqueous alkali in an amount sufficient to carry out the reacting step.

5. The method of claim 1, wherein the lutein-containing extract comprises lutein in saponified or esterified form.

6. The method of claim 1, wherein the lutein-containing extract also comprises other xanthophylls or carotenoids.

7. The method of claim 1, wherein the reacting step is conducted under vacuum.

8. The method of claim 1, wherein from about 10% to 50% non-aqueous alkali, by weight of the total mixture, is added to said mixture.

9. The method of claim 1, wherein from about 15% to 30% non-aqueous alkali, by weight of the total mixture, is added to said mixture.

10. The method of claim 1, wherein from about 8% to 20% non-aqueous alkali, by weight, is added to saponify the mixture, and from about 1% to 30% additional non-aqueous alkali, by weight of the final mixture is added to effect isomerization.

11. The method of claim 1, wherein the alkali is selected from the group consisting of a metal hydroxide, a metal carbonate, ammonium hydroxide, ammonia, an organic base and a mixture of the foregoing.

12. The method of claim 1, wherein the first step of adding non-aqueous alkali is followed by a saponification reaction conducted at a temperature different than the reacting step.

13. The method of claim 1, wherein the reacting step is conducted for a time between about 5 minutes and about 300 hours.

14. The method of claim 1, wherein the reacting step is conducted for a time between about 1 hour and about 50 hours.

15. The method of claim 1, wherein the reacting step is conducted for a time between about 2 hours and about 25 hours.

16. The method of claim 1, wherein the reacting step is conducted for a time between about 3 hours and about 10 hours.

17. The method of claim 1, wherein the reacting step is carried out at atmospheric pressure, or from about 5 psi to about 150 psi pressure.

18. The method of claim 1, wherein the reacting step is conducted at a temperature between about 25° C. and about 180° C.

19. The method of claim 1, wherein the reacting step is conducted at a temperature between about 50° C. and about 150° C.

20. The method of claim 1, wherein the reacting step is conducted at a temperature between about 60° C. and about 120° C.

21. The method of claim 12, wherein the saponification reaction is conducted at a temperature between about 25° and about 100°.

22. The method of claim 1, wherein the mixture of zeaxanthin epimers obtained represents from 6% to 90% of the total carotenoids.

* * * * *